(12) United States Patent
Sabatini et al.

(10) Patent No.: US 9,226,509 B2
(45) Date of Patent: Jan. 5, 2016

(54) PHAGODETERRENT COMPOUNDS OF FUNGAL ORIGIN

(75) Inventors: Maria Agnese Sabatini, Modena (IT); Sonia Ganassi, Modena (IT); Claudio Altomare, Bari (IT); Mara Favilla, Bari (IT); Antonio Evidente, Napoli (IT); Anna Andolfi, Napoli (IT)

(73) Assignee: Consiglio Nazionale Delle Ricerche, Rome (IT)

( * ) Notice: Subject to any disclaimer, the term of this patent is extended or adjusted under 35 U.S.C. 154(b) by 0 days.

(21) Appl. No.: 14/117,349

(22) PCT Filed: May 14, 2012

(86) PCT No.: PCT/IB2012/052383
§ 371 (c)(1),
(2), (4) Date: Nov. 12, 2013

(87) PCT Pub. No.: WO2012/153314
PCT Pub. Date: Nov. 15, 2012

(65) Prior Publication Data
US 2014/0228448 A1 Aug. 14, 2014

(30) Foreign Application Priority Data
May 12, 2011 (IT) .............................. MI2011A0831

(51) Int. Cl.
*A01N 31/00* (2006.01)
*A01N 63/04* (2006.01)
*A01N 31/02* (2006.01)

(52) U.S. Cl.
CPC ................ *A01N 63/04* (2013.01); *A01N 31/02* (2013.01); *A01N 31/00* (2013.01)

(58) Field of Classification Search
CPC ....... A01N 31/02; A01N 31/00; A01N 25/04; A01N 27/00; A01N 65/00
See application file for complete search history.

(56) References Cited

U.S. PATENT DOCUMENTS

| | | | |
|---|---|---|---|
| 5,614,196 A | | 3/1997 | Norris et al. |
| 2009/0257959 A1* | | 10/2009 | Sims ............................. 424/45 |

OTHER PUBLICATIONS

Hosozawa et al., "Antifeeding Active Substances for Insect in Plant," Agricultural and Biological Chemistry 38(5):1045-1048 (1974).
Martin et al., "Comparative Chemistry and Insect Antifeedant Action of Traditional (Clevenger and Soxhlet) and Supercritical Extracts (CO2) of Two Cultivated Wormwood (*Artemisia absinthium* L.) Populations," Industrial Crops and Products 34:1615-1621 (2011).
Evidente et al., "Citrantifidiene and Citrantifidiol: Bioactive Metabolites Produced by Trichoderma citrinoviride with Potential Antifeedant Activity Towards Aphids," Journal of Agricultural and Food Chemistry 56:3569-3573.
Ganassi et al., "Detection of Fungal Metabolites of Various *Trichoderma* Species by the Aphid *Schizaphis graminum*," Entomologia Experimentalis et Applicata 122:77-86 (2007).
Jacobson et al., "Boll Weevil Feeding Deterrents from Tung Oil," Journal of Agricultural and Food Chemistry 29:591-593 (1981).
International Search Report and Written Opinion for PCT/IB2012/052383, filed May 14, 2012 (mailed Oct. 5, 2012).

\* cited by examiner

*Primary Examiner* — Kevin E Weddington
(74) *Attorney, Agent, or Firm* — LeClairRyan, a Professional Corporation

(57) ABSTRACT

The present invention relates to the use of R—OH alcohols as phagodeterrents, and to a method for treating plants infested with aphids which comprises the administration of these R—OH alcohols.

7 Claims, No Drawings

PHAGODETERRENT COMPOUNDS OF FUNGAL ORIGIN

This application is a national stage application under 35 U.S.C. §371 of PCT Application No. PCT/IB2012/052383, filed May 14, 2012, which claims the priority benefit of Italian Patent Application No. MI2011A000831, filed May 12, 2011.

FIELD OF THE INVENTION

The present invention relates to compounds of fungal origin to be used as phagodeterrents for aphids, and methods for treating plants infested thereby.

STATE OF THE ART

Aphid control is still today for the most part based on the use of synthetic chemical substances: phospho-organic and chloro-organic compounds, and neonicotinoids. The first two groups include substances having aphicidal activity which act primarily through contact and asphyxia. Although the majority of chloro-organic products do not induce acute intoxication in humans at the doses used, they can accumulate within the body, thus giving rise to chronic intoxications in humans and in other vertebrates. As regards phospho-organic compounds, their toxicity in vertebrates, humans in particular, is variable, often becoming very high. However, contrary to chlorine derivatives, phospho-organic compounds are not very stable, in fact their degradation occurs in a short time (from only a few hours to a few days or weeks).

Neonicotinoids are among the most recently used insecticides: the advantages of these synthetic molecules include low toxicity for humans and other vertebrates, and the possibility of using them as "systemic", in that they enter the lymphatic system of plants, thus explaining why they are also lethal for insects which feed on lymph, such as aphids. However, in various areas of the world, lethal and sub-lethal effects of these products on "useful" insects, such as phytophage predators (ladybirds), parasitoids, wild bees and bumblebees have been recorded and described. Furthermore, phenomena of resistance to these phytopharmaceuticals are becoming increasingly common, even in response to the most recently synthesised neonicotinoids, which in some cases are no longer capable of controlling parasite populations.

The phytopharmaceuticals having insecticidal properties against aphids include those derived directly from plants or their products, such as pyrethrin, rotenone and azadirachtin.

Pyrethroids, which have been initially synthesised by starting from some of the components of pyrethrins, act by contact, penetrating through the integument and causing paralysis and death of the insects. Commercially available products based on pyrethroids have the advantage of being effective against insects at low dosages and having a very short-lived persistence within the environment, because they are rapidly inactivated. Disadvantageously, however, as already observed for neonicotinoids, also these phytopharmaceuticals are lethal for the insects "useful" against phytophages.

In nature, various organisms, both of animal and of fungal origin, fight aphids. Some of these organisms are already being used in the field and are commercially available. Among the natural enemies of aphids, that are already commercially available, predators can be cited, such as: oleopters coccinellidae (*Adalia bipunctata, Coccinella septempunctata,* and *Coccinella decempunctata*); anthocorid hemiptera (species of the genera *Orius* and *Anthocoris*); neuroptera chrysopidae (species of the genera *Chrysopa* and *Chrysoperla*); diptera syrphidae: *Syrphus* spp., parasitoids, such as diptera cecidomyiidae (*Aphidoletes* spp.) and the hymenoptera aphididae (*Aphidus* spp.), and fungi, such as *Verticillium lecanii*, *Lecanicillium lecanii*, *Metarhizium anisopliae* and *Beauveria bassiana*. However, the major difficulty in using the above-mentioned organisms or natural substances of vegetable origin is ascribable to the extremely variable possibilities of performing a suitable reduction of the aphid populations.

The adverse effects of synthesised phytopharmaceuticals, and the unsatisfactory results obtained so far with biocontrol strategies compromise the possibility of limiting the damage to phytophagous organisms.

The object of the present invention is therefore to provide compounds which have phagodeterrent characteristics and do not present the above drawbacks of the known compounds for the same application.

SUMMARY OF THE INVENTION

The above object has been achieved through the use of a primary alcohol of formula R—OH, wherein R is an unbranched, unsubstituted linear aliphatic group having 10 to 24 carbon atoms, saturated or unsaturated having up to two cis double bonds, as phagodeterrent.

In another aspect, the invention relates to a method for treating plants against aphid infestations, comprising the step of administering an aqueous suspension of said at least one R—OH alcohol.

In a still further aspect, the invention relates to a phagodeterrent composition comprising at least one primary alcohol of formula R—OH, wherein R is an unbranched, unsubstituted linear aliphatic group having 10 to 24 carbon atoms, saturated or unsaturated having up to two cis double bonds, and at least one between citrantifidiene and citrantifidiol.

The characteristics and the advantages of the present invention will be clear from the following detailed description and working examples provided for illustrative and non-limiting purposes.

DETAILED DESCRIPTION OF THE INVENTION

The invention therefore relates to the use of a primary alcohol of formula R—OH, wherein R is an unbranched, unsubstituted linear aliphatic group having 10 to 24 carbon atoms, saturated or unsaturated having up to two cis double bonds, as phagodeterrent.

In particular, the expression "unsaturated having up to two cis double bonds" means that, when the R group is unsaturated, the R group contains only cis double bonds and only in a number not higher than 2.

As will indeed be clear from the examples given below, such an R—OH alcohol has proved to be surprisingly effective as an aphid deterrent on plants infested or potentially subject to infestations.

Said R—OH alcohol is preferably selected from dodecanol, tridecanol, tetradecanol, pentadecanol, hexadecanol, cis-9-hexadecenol, heptadecanol, octadecanol, cis-9-octadecenol, 16-methylheptadecanol, cis, cis-9,12-octadecadienol, nonadecanol, eicosanol, eneicosanol, dosanol, tricosanol, and tetracosanol.

Preferably, said R—OH alcohol has from 12 to 18 carbon atoms.

According to a preferred embodiment, said R—OH alcohol is of natural fungal origin, in that it is extracted from the fungus *Trichoderma citrinoviride*.

In another aspect, the present invention relates to a method of treating plants against aphid infestations, comprising the step of administering an aqueous suspension of at least one primary alcohol of formula R—OH, wherein R is an unbranched unsubstituted linear aliphatic group having 10 to 24 carbon atoms, saturated or unsaturated having up to two cis double bonds. Surprisingly, it has in fact been observed that aqueous suspensions of one or more of said R—OH alcohols enable the aphids to be dissuaded, thus exerting an effective deterrent action without causing their death and at the same time without causing the death of insects “useful” against phytophages.

Preferably, in said aqueous suspension, said at least one R—OH alcohol is in a concentration of 0.05 mM to 3 mM, more preferably 0.1 mM to 2 mM. Indeed, it has been advantageously observed that significantly reduced concentrations are sufficient to obtain surprisingly satisfactory results.

According to a preferred embodiment, said at least one R—OH alcohol is of natural fungal origin, in that it is extracted from the fungus *Trichoderma citrinoviride*.

Said aqueous suspension is preferably an aqueous solution of 2-5% vol/vol of methanol, wherein said at least one R—OH alcohol is suspended.

Said at least one R—OH alcohol is preferably selected from dodecanol, tridecanol, tetradecanol, pentadecanol, hexadecanol, cis-9-hexadecenol, heptadecanol, octadecanol, cis-9-octadecenol, 16-methylheptadecanol, cis,cis-9,12-octadecadienol, nonadecanol, eicosanol, eneicosanol, dosanol, tricosanol, and tetracosanol.

Preferably, said at least one R—OH alcohol has 12 to 18 carbon atoms.

According to a preferred embodiment, 2 to 5 different R—OH alcohols are present in said aqueous suspension. More preferably, said 2 to 5 different R—OH alcohols are selected from tetradecanol, pentadecanol, hexadecanol, heptadecanol, octadecanol, and cis-9-octadecenol.

According to another preferred embodiment, said aqueous suspension further comprises citrantifidiene, citrantifidiol or mixtures thereof.

Citrantifidiene is the dimethyl ester of 2,5-bis-(2-hydroxyethyl)-hexa-2,4-dienedienoic acid of formula:

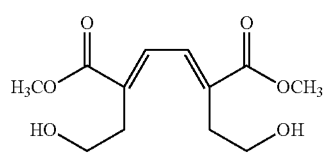 [SMILES: COC(=O)/C(=C/C=C(\CCO)C(=O)OC)CCO]

whereas citrantifidiol is a fourfold substituted cyclohexane-1,3-diol of formula:

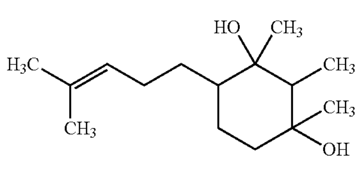 [SMILES: CC(C)=CCCC1CCC(C)(O)C(C)C1(C)O]

Both these further compounds are preferably extracted from the fungus *Trichoderma citrinoviride*.

Indeed, by combining at least one R—OH alcohol, according to the present invention, with at least one of citrantifidiene and citrantifidiol it is possible to increase the phagodeterrence against aphids.

In a further aspect, the present invention therefore relates to a phagodeterrent composition comprising at least one primary alcohol of formula R—OH, wherein R is an unbranched, unsubstituted linear aliphatic group having 10 to 24 carbon atoms, saturated or unsaturated having up to two cis double bonds, and at least one between citrantifidiene and citrantifidiol.

Working examples of the present invention are provided below for illustrative purposes.

EXAMPLES

Example 1

Extraction of Metabolites from the Fungal *Trichoderma citrinoviride* Strain As this fungus showed a phagodeterrent capacity, the first aim was to identify the metabolites responsible for this activity. This Example therefore reports the work carried out on the extraction and characterisation of these metabolites.

In order to produce biomass and extract the metabolites, the *Trichoderma citrinoviride* strain ITEM 4484 was cultivated on solid substrate. 200 g of rice with about 45 wt % of moisture content and sterilised in an autoclave in a 500-ml Erlenmeyer flask was inoculated with 10-15 pieces (2×2 mm) of a fresh (5-7 day-old) culture of fungus on potato-dextrose-agar (PDA). The cultures were incubated at 25° C. for 4 weeks with an alternating 12-h light-dark cycle. The biomass was then harvested and dried in a ventilated oven at 35° C. for 48 h, and finally it was finely ground in a laboratory mill (Molino Cyclone LMLF; PBI International, Milan, Italy), to obtain particles of less than 0.2 mm in size. The biomass thus obtained was stored at −20° C. until extraction of the metabolites.

The solid fungal culture (1 kg) was then homogenised in a blender (Waring, Torrington, Conn.) for a few minutes with approximately 5 litres of a mixture composed of MeOH—$H_2O$ (1% NaCl) (55:45 v/v). The suspension obtained was centrifuged at 10 000 g for 40 minutes. The supernatant was first degreased with n-hexane (2×2.5 I) and then re-extracted with $CH_2Cl_3$ (3×2.5 I). The entire procedure was repeated a second time on the solid phase using a volume of MeOH—$H_2O$ (1% NaCl) (55:45 v/v) equal to ⅔ of the initial volume. The organic extracts were recombined and anhydrified with anhydrous $Na_2SO_4$, filtered and evaporated at reduced pressure, producing a residue consisting of abundant brown oil (15 g). The residual organic extract obtained was analysed by TLC on silica-gel plates using the chloroform-isopropanol mixture (85:15 v/v) as the eluent.

The organic extract of the *Trichoderma citrinoviride* culture (15 g) was chromatographed on a silica-gel chromatography column under room pressure using the chloroform-isopropanol mixture (85:15 v/v) as the eluent, followed by final elution with methanol. 10 groups of homogenous fractions (A-L) were obtained, which were analysed by TLC on silica-gel plates using the same eluent system. The purification was monitored by assaying the activity of the fractions obtained at each stage. The third fraction (C1.284 g), which has proved to be active in the behavioural assays, was purified through a chromatographic column of silica gel by using the chloroform-isopropanol mixture (9:1 v/v) as the eluent. 9 groups of homogenous fractions were obtained. The fraction named C2 (80.1 mg) was purified through two successive stages of silica-gel TLC and by using the petroleum ether-acetone mixture (9:1 v/v) as the eluent, thus forming a mixture containing the metabolites (5.4 mg, Rf 0.29, eluent petroleum ether-acetone (9:1 v/v) 5.4 mg/kg).

Characterisation of the Metabolites Extracted from the *Trichoderma citrinoviride* Strain The IR spectrum (Perkin-Elmer Spectrum One FT-IR, Norwalk, Conn.) of the metabolite mixture showed the presence of various bands typical of some functional groups, such as:

- a band at 3349 cm$^{-1}$ typical of the stretching vibration of the O—H bond of hydroxyl groups;
- a band at 2922 cm$^{-1}$ typical of the stretching vibration of the $CH_2$ groups;
- a band at 2852 cm$^{-1}$ typical of the stretching vibration of the $CH_3$ groups; and
- a band at 1466 cm$^{-1}$ typical of the bending vibration of the $CH_3$ groups.

The UV spectrum (Perkin-Elmer Lamda 25 UV-VIS) showed only the final absorption: $\lambda_{max}$<200.

The $^1$H-NMR spectrum (Bruker, Karlsruhe, Germany) showed the following signals at δ: 5.38 (m); 5.35 (m); 3.64 (t, J=6.3 Hz); 2.01 (m); 2.00 (m); 1.57-1.26 (m); 0.88 (t, J=6.8 Hz) (Pretsch et al., 2000).

The $^{13}$C-NMR spectrum showed the following signals at δ: 130.5 (d); 130.3 (d); 129.9 (d); 129.8 (d); 63.1 (t) 32.8-22.7 (t); 14.1 (q) (Breitmaier and Voelter, 1987).

The ESI-MS spectrum (Waters Micromass Q-TOF Micro (Milford, Miss.) (recorded in positive modality) showed the following peaks at m/z: 265 $[M_{C16}+Na]^+$; 293 $[M_{C18}+Na]^+$; 291 $[M_{C18}:1_{\Delta 9}+Na]^+$.

These data enable the identification in the mixture of 4 R—OH alcohols (C:16 and C:18) both saturated and unsaturated.

GC-MS Analysis of the Metabolites

The presence of saturated and unsaturated R—OH alcohols in the extracted mixture was confirmed by the following chemical and GC-MS investigations.

The metabolites were oxidised using Jones reactant in the respective acids and the latter were converted into the related methyl ethers by reacting with diazo-methane. The mixture of the esters thus obtained was subjected to GC-MS analysis through a QP5050 Shimadzu instrument by using a Supleco-wax TM10 column measuring 60 m×0.32, 0.5 μm. The conditions used for the GC analysis were as follows: carrier gas, helium at a flow velocity of 2.1 ml/min, initial pressure 52 Kpa; column temperature, initial 180° C. for 15 minutes, incrementing by 10° C./min to 230° C. for 20 minutes; split injector temperature 270° C. The conditions used for the MS analysis were as follows: electron-impact Ion source, 70 eV; interface temperature 270° C., ion source temperature 200° C.; mass range from 40 to 450 amu; scanning velocity, 0.5 scans/sec.

The GC chromatogram showed the presence of peaks at retention times corresponding to those of methyl esters of the following R—OH alcohols: C 16:0, C 18:0, C 18:1 Δ9c and C 18:1 Δ9t. These results were confirmed by the data obtained from the EI-MS spectra, which showed molecular ion peaks and fragmentation peaks typical of these compounds. GC-MS analysis also provided the percentage of the following alcohols: C 16:0 39.0%; C 18:0 16.0%; C18:1 Δ9c 20.5% and C 18:1 Δ9t 22.5%.

Therefore, on the basis of these data, the metabolite mixture extracted from the fungus *Trichoderma citrinoviride* was shown to be composed of:
- 16.20% hexadecanol
- 39.0% octadecanol
- 22.5% cis-9-octadecenol
- 22.5% trans-9-octadecenol Example 2

Evaluation of the Phagodeterrent Activity of Metabolites Extracted from the *Trichoderma citrinoviride* Strain and of Other R—OH Alcohols For evaluating the phagodeterrent activity against aphids, the individual R—OH alcohols were firstly studied.

In this regard, tests were conducted not only on R—OH alcohols extracted from the *Trichoderma citrinoviride* strain, but also on other R—OH alcohols, as shown in Table 1 and the procedure below.

Leaf Treatment:

Treatment of wheat leaves consisted of immersion of the same for 10 seconds in aqueous suspensions of 5% methanol of the different alcohols, some of which were also tested at different concentrations.

As a control, the same number of leaves was prepared by immersion in an aqueous solution of 5% methanol only.

Assay of the Phaqodeterrent Activity of the R—OH Alcohols:

Petri dishes 9 cm in diameter were used, into each of which two wheat leaves were arranged in parallel and separated from one another by a distance of approximately 4 cm; one leaf was treated with the suspension in 5% methanol of alcohol at various concentrations, and the other control leaf was washed with a solution of 5% methanol. Aphids of the species *Rhopalosiphum padi* were introduced to the dishes (one per dish) at equal distance from the two leaves.

For each test, 10 aphids were used and the same test was repeated at least 12 times, for at least 120 aphids. The number of aphids present on the treated leaves and on the control leaves was recorded each hour for a total of 8 hours.

The raw data relating to the food choices of the aphids were analysed using the Generalised Linear Model (GLM) procedure for repeated measurements (SPSS release 15.01) and reported in Table 1. The differences of the media between the number of aphids per leaf at each temperature and the number of aphids on corresponding control leaves were analysed and corrected by using the Bonferroni test for multiple comparisons.

TABLE 1

Effect of the R—OH alcohols at different concentrations on food preferences of the aphid *Rhopalosiphum padi*

| Alcohols tested | GLM: treatment time* | | Bonferroni test | | |
|---|---|---|---|---|---|
| | | | Treated media | Control media | |
| Tetradecanol (1.2 mM) | $F_{7,154}$ = 4.230 | P < 0.01 | 1.938 ± 0.322 | 6.271 ± 0.322 | ** |
| Tetradecanol (0.6 mM) | $F_{7,154}$ = 2.318 | P < 0.05 | 2.365 ± 0.264 | 5.292 ± 0.264 | ** |
| Tetradecanol (0.3 mM) | $F_{7,154}$ = 1.186 | P > 0.05 | 3.271 ± 0.217 | 5.552 ± 0.217 | ** |
| Tetradecanol (0.15 mM) | $F_{7,154}$ = 10.72 | P < 0.01 | 2.375 ± 0.370 | 5.980 ± 0.370 | ** |
| Pentadecanol (1.2 mM) | $F_{7,154}$ = 2.354 | P < 0.05 | 1.365 ± 0.301 | 7.615 ± 0.301 | ** |
| Pentadecanol (0.6 mM) | $F_{7,154}$ = 11.052 | P < 0.01 | 2.385 ± 0.237 | 6.188 ± 0.237 | ** |

TABLE 1-continued

Effect of the R—OH alcohols at different concentrations on food preferences of the aphid *Rhopalosiphum padi*

| Alcohols tested | GLM: treatment time* | | Bonferroni test | | |
|---|---|---|---|---|---|
| | | | Treated media | Control media | |
| Pentadecanol (0.3 mM) | $F_{7,154} = 4.686$ | P < 0.01 | 2.271 ± 0.283 | 6.292 ± 0.283 | ** |
| Pentadecanol (0.15 mM) | $F_{7,154} = 4.265$ | P < 0.01 | 3.406 ± 0.405 | 5.083 ± 0.405 | ** |
| Pentadecanol (0.075 mM) | $F_{7,154} = 1.576$ | P > 0.05 | 3.073 ± 0.335 | 5.594 ± 0.335 | ** |
| Hexadecanol (1.2 mM) | $F_{7,196} = 5.488$ | P < 0.01 | 1.308 ± 0.315 | 7.717 ± 0.315 | ** |
| Hexadecanol (0.6 mM) | $F_{7,154} = 4.367$ | P < 0.01 | 2.281 ± 0.371 | 6.531 ± 0.371 | ** |
| Hexadecanol (0.3 mM) | $F_{7,154} = 1.336$ | P > 0.05 | 2.635 ± 0.323 | 6.635 ± 0.323 | ** |
| Hexadecanol (0.15 mM) | $F_{7,154} = 2.837$ | P < 0.01 | 3.938 ± 0.429 | 5.479 ± 0.429 | * |
| Heptadecanol (1.2 mM) | $F_{7,154} = 6.940$ | P < 0.01 | 1.094 ± 0.294 | 6.427 ± 0.294 | ** |
| Heptadecanol (0.6 mM) | $F_{7,154} = 0.863$ | P > 0.05 | 2.177 ± 0.298 | 5.240 ± 0.298 | ** |
| Heptadecanol (0.3 mM) | $F_{7,154} = 1.265$ | P > 0.05 | 3.063 ± 0.532 | 5.448 ± 0.532 | ** |
| Heptadecanol (0.15 mM) | $F_{7,154} = 2.892$ | P < 0.01 | 3.240 ± 0.410 | 5.677 ± 0.410 | ** |
| Octadecenol (1.2 mM) | $F_{7,154} = 0.863$ | P > 0.05 | 2.469 ± 0.333 | 5.927 ± 0.333 | ** |
| Cis-9-octadecenol (1.2 mM) | $F_{7,154} = 8.443$ | P < 0.01 | 2.281 ± 0.283 | 7.177 ± 0.283 | ** |
| Nonadecanol (1.2 mM) | $F_{7,154} = 1.573$ | P > 0.05 | 3.427 ± 0.391 | 4.792 ± 0.391 | * |
| Eicosanol (1.2 mM) | $F_{7,154} = 5.048$ | P < 0.01 | 3.042 ± 0.303 | 5.073 ± 0.303 | ** |

(*P < 0.05; ** P < 0.01)

For all the above-mentioned tests, the mean number of aphids on the treated leaves in the Bonferroni test was significantly lower than that for the respective controls throughout the duration of the test. Therefore, the phagodeterrent effectiveness of the R—OH alcohols of the invention was demonstrated even at advantageously low concentrations.

From the detailed description and the Examples given above, the advantages resulting from the use of the R—OH alcohols of the present invention are clear. In particular, these compounds have been shown to be surprisingly and advantageously suitable for use as phagodeterrents. At the same time, since they are non-toxic and extremely easy to handle, these compounds are convenient to be used in the open-field, and on very extensive areas of agricultural land.

The invention claimed is:

1. A method of treating plants against aphid infestation, comprising the step of administering an aqueous suspension of at least one primary alcohol of formula R—OH, wherein R is an unbranched, unsubstituted linear aliphatic group having 10 to 24 carbon atoms, saturated or unsaturated having up to two cis double bonds, wherein the at least one primary alcohol is a phagodeterrent agent.

2. The method of claim 1, wherein said at least one R—OH alcohol is in a concentration of 0.05 mM to 3 mM, preferably 0.1 mM to 2 mM.

3. The method of claim 2, wherein said at least one R—OH alcohol is extracted from fungus *Trichoderma citrinoviride*.

4. The method of claim 1, wherein said aqueous suspension is an aqueous solution of methanol 2-5% vol/vol, wherein said at least one R—OH alcohol is suspended.

5. The method of claim 1, wherein 2 to 5 R—OH alcohols are present in said aqueous suspension.

6. The method of claim 5, wherein said 2 to 5 R—OH alcohols are selected from tetradecanol, pentadecanol, hexadecanol, heptadecanol, octadecanol, and cis-9-octadecenol.

7. The method of claim 1, wherein said aqueous suspension further comprises citrantifidiene, citrantifidiol or a mixture thereof.

* * * * *